United States Patent [19]

Curtis

[11] Patent Number: 5,092,677
[45] Date of Patent: Mar. 3, 1992

[54] PHOTOMETER HAVING A LONG LAMP LIFE, REDUCED WARM-UP PERIOD AND RESONANT FREQUENCY MIXING

[75] Inventor: Richard Curtis, Gorham, Me.

[73] Assignee: Artel, Inc., South Windham, Me.

[21] Appl. No.: 388,661

[22] Filed: Aug. 2, 1989

[51] Int. Cl.$^5$ .................................... G01N 21/25
[52] U.S. Cl. .............................. 356/414; 356/435; 250/565; 313/637
[58] Field of Search ............... 356/319, 414, 435; 313/637, 643, 641; 250/575, 565

[56] References Cited

U.S. PATENT DOCUMENTS

| | | | |
|---|---|---|---|
| 2,326,878 | 8/1943 | Müller | 88/14 |
| 3,537,794 | 11/1970 | Louder | 356/40 |
| 3,656,856 | 4/1972 | Katz et al. | 356/206 |
| 3,703,336 | 11/1972 | Rosse et al. | 356/39 |
| 3,836,333 | 9/1974 | Mintz | 23/259 |
| 3,859,539 | 1/1975 | Allington | 250/575 |
| 4,229,104 | 10/1980 | Lahme et al. | 356/246 |
| 4,329,062 | 5/1982 | Harr et al. | 356/414 |
| 4,409,517 | 10/1983 | Van Der Sande et al. | 313/637 |
| 4,412,744 | 11/1983 | Lee et al. | 356/319 |
| 4,529,912 | 7/1985 | Northrup et al. | 315/117 |
| 4,536,091 | 8/1985 | Allington | 356/435 |
| 4,560,269 | 12/1985 | Baldszun et al. | 356/246 |
| 4,565,447 | 1/1986 | Nelson | 356/319 |
| 4,575,240 | 3/1986 | Hess et al. | 356/246 |
| 4,590,367 | 5/1986 | Ross et al. | 250/205 |

OTHER PUBLICATIONS

Defreese et al., "Simultaneous, Split-Beam, Ratio Measurement System," Analytical Chemistry, vol. 48, No. 11, Sep. 1976.
Pardue et al., "High-Stability Photometer Utilizing Feedback", Analytical Chemistry, vol. 39, No. 8, Jul. 1967.

Primary Examiner—Vincent P. McGraw
Assistant Examiner—LaCharles P. Keesee
Attorney, Agent, or Firm—Wolf, Greenfield & Sacks

[57] ABSTRACT

An apparatus and method for making a photometric determination regarding the contents of a sample, such as the absorbance characteristic of a blood serum sample. The improvement allows measurements to be taken after a reduced warm-up period and compensates for variations in the lamp intensity during the period over which measurements are taken. A feedback circuit is provided between a reference photodetector and the light source for causing the light source intensity to asymptotically approach a final stable value in a smooth exponential curve. Signal processing means processes outputs of the reference and sample photodetectors taken at different times so as to compensate for variations in the source intensity over the time period during which the outputs are taken. Still further, the photometer allows resonant frequency mixing of the contents of a cuvette while disposed in the photometer by causing the entire optical assembly, in which the cuvette is mounted, to vibrate at its resonant frequency. A microprocessor-controlled search routine is used to determine the resonant frequency of the optical assembly which is easily recalculated each time there is a change in the dimensions or mass of the optical assembly, or in the contents of the cuvette.

11 Claims, 7 Drawing Sheets

PHOTOMETER HAVING A LONG LAMP LIFE, REDUCED WARM-UP PERIOD AND RESONANT FREQUENCY MIXING

BACKGROUND OF THE INVENTION

The present invention concerns a photometer for performing measurements at various wavelengths and which allows measurements to be made after a short warm up period, thus increasing the throughput of the system and extending the useable lifetime of the light source The system also allows resonant frequency mixing of the sample for increasing the throughput of the system and the accuracy of the measurements.

Photometers have been used for performing analysis of various analytes. In one application, a reagent tablet and diluent are inserted into a cuvette and mixed until the reagent tablet dissolves in the diluent. The mixing may be done with a stirring rod inserted into the cuvette, or by oscillating the cuvette in an off line shaker. The sample to be analyzed, such as blood serum, is then added to the cuvette and again mixed. After the contents are added to the cuvette it is often desirable to warm the contents to a highly precise temperature. The mixing action promotes highly effective heat transfer between the heater surrounding the cuvette and the cuvette contents so that the temperature of the contents achieves stability much more quickly. The cuvette is then inserted into a holder within the photometer and a photometric analysis of the reaction product is performed.

Some of the principle disadvantages of known photometers are the extended warm up period required to stabilize the output of the light source before a measurement can be taken and the short lifetime of the lamp bulb. Furthermore, off-line mixing of the cuvette contents requires additional handling by the operator and is inefficient—i.e., it allows the contents of the cuvette to cool during transfer from the mixing instrument to the measuring instrument and allows partial settlement before a measurement can be taken.

For example, a problem with the prior art tungsten filament bulb in applications requiring a measurement near the ultraviolet spectrum is that the filament is required to run at temperatures above 2900° K. This high temperature limits the life of the bulb due to evaporation of tungsten from the filament and its deposition on the inner surface of the bulb. The filament is weakened by this evaporation and as the bulb is blackened, less light is emitted from the bulb.

One prior art solution has been to utilize a tungsten filament bulb filled with halogen gas e.g., bromine or iodine. A chemical reaction between the tungsten and halogen removes the tungsten from the surface of the bulb and redeposits it on the filament. This increases the life of the bulb. However, a disadvantage is that the bulb must be on for at least fifteen minutes to bring it up to full temperature (bulb temperature of 250° C.) for the halogen redeposition to take place. Still further, the emitted light intensity does not stabilize until the bulb is fully warmed and stable, typically about 15-30 minutes. Thus, the halogen bulb is generally left on for long periods of time between measurements, resulting in a reduced useful bulb life.

It is an object of this invention to provide a photometer capable of performing chemical and immunochemical assays on a broad array of analytes.

Another object is to provide the fastest possible warm up of the cuvette contents to a highly precise temperature A further object is to provide a photometer which allows measurements to be taken after a short warm up period, thus allowing the light source to be turned off between measurements and extending the useful lifetime of the source.

A still further object is to provide a photometer which provides vigorous mixing of the contents of the cuvette and which allows ready determination of the optimum mixing frequency.

SUMMARY OF THE INVENTION

The invention concerns an apparatus and method for making photometric measurements regarding the contents of a sample, such as the absorbance of a liquid solution. An important application is the performance of chemical and immunochemical assays on blood serum samples for a broad array of analytes, such as glucose, albumin, cholesterol, etc.

The apparatus and method of this invention causes the lamp output to stabilize more quickly, and furthermore allows a photometric measurement to be made before the light source intensity is fully stable. A feedback circuit provided between a light source and a reference photometer causes the source intensity to stabilize more quickly and to asymptotically approach a final stable value in a smooth exponential curve.

A tungsten filament bulb filled with an inert gas is used as the light source. The gas, preferably krypton or argon, has a low thermal conductivity and minimizes evaporation of tungsten atoms from the filament. The lamp does not require redeposition of tungsten on the filament and thus the long warm up period required for redeposition is avoided. Because of the reduced warm up period, the lamp can be turned off between readings and the useful bulb life is thus significantly extended. A typical reading duration is about five seconds.

Before the intensity has reached its final stable value, a measurement can be taken and any approximately linear variation in the intensity during the time period over which the measurement is made is compensated for by special processing of the outputs of the reference and sample photodetectors. In a preferred embodiment, a processor containing a software algorithm receives four outputs taken in series at different times from the reference and sample photometers. Two reference measurements (from the reference photodetector) are made at equal times before and after a midpoint in time; likewise, two sample measurements (from the sample photodetector) are made at equal times before and after the midpoint. By averaging the two reference measurements, averaging the two sample measurements, and taking the ratio thereof, an accurate determination of sample absorbance is obtained as if all measurements were all taken at the same point in time.

The photometer of this invention further provides improved mixing of the contents of the cuvette. In a preferred embodiment, the entire optical assembly of the photometer, including a cuvette holder, is vibrated at its resonant frequency. Electromechanical coupling elements are provided for driving the optical assembly at its resonant frequency and a motion detector monitors the movement of the optical assembly. A microprocessor controlled search routine determines the resonant frequency of the optical assembly and stores the same for its subsequent use. The output of the motion detector is processed to calculate the resonant frequency and signals the microprocessor to recalculate the resonant frequency if insufficient motion is detected.

DETAILED DESCRIPTION OF THE PREFERRED EMBODIMENT

Figure 1:
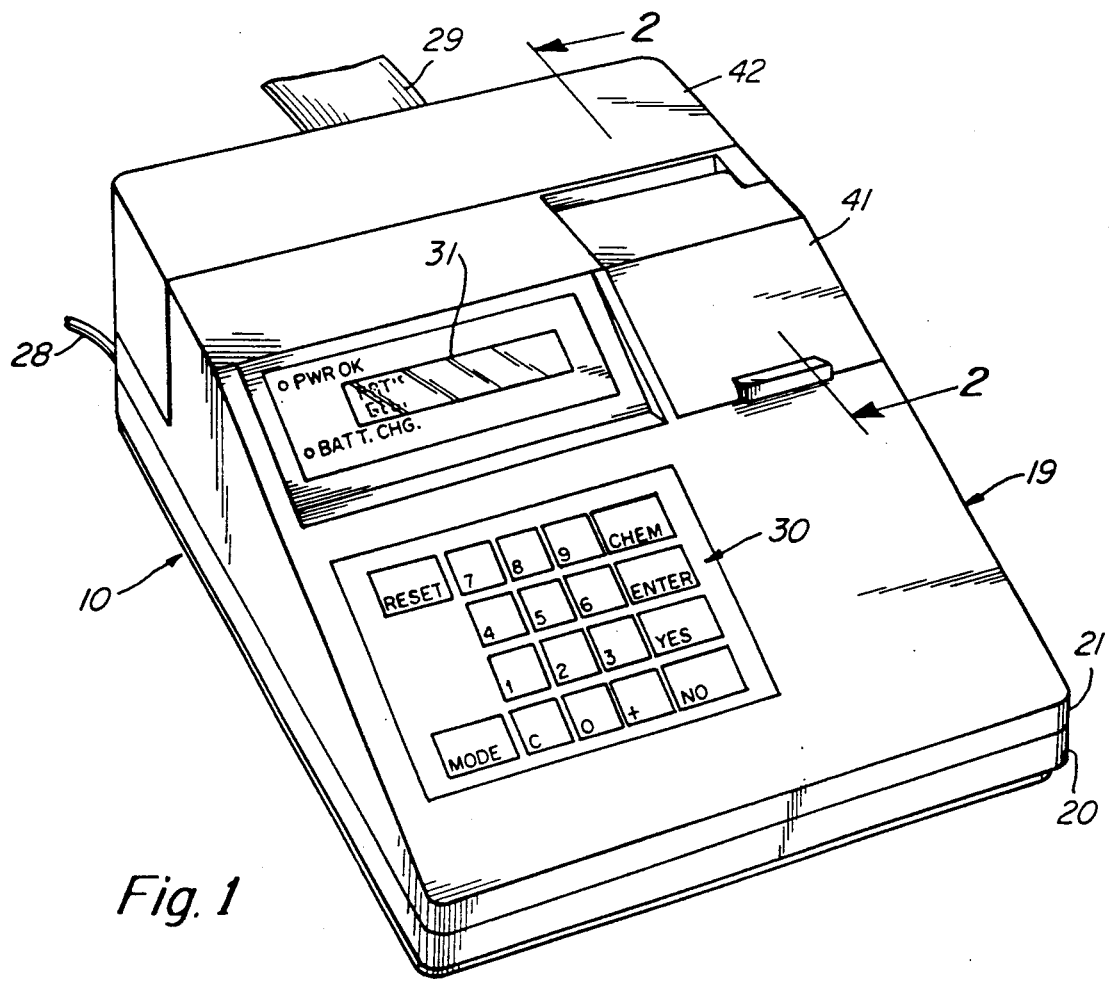
FIG. 1 is a top perspective view of the photometer instrument of this invention.

The photometer instrument 10 shown in FIG. 1 is part of a one test at a time system for performing chemical and immunochemical assays on a broad array of analytes. The system further includes reagents in liquid or tablet form, diluent, and disposable cuvettes. An important application is the analysis of blood serum samples for glucose, albumin, cholesterol, etc.

The instrument 10 is a wavelength selectable photometer with the ability to handle the dissolving, mixing, heating and photometric measurement requirements of an assay. The instrument is operated via a top panel keypad 30 (see FIG. 1). It communicates information to the operator via an alpha numeric LCD display 31, an optional printer output (not shown), and through audible and visual signals at specific points during, and at the conclusion of, each analysis.

Following verification that the instrument is ready for an analysis, information that defines the assay to be run and the patient s ID number are entered on the keypad 30. A cuvette 27 (see FIG. 2) filled with a reagent tablet and diluent is mixed and heated in the instrument. A photometric calibration measurement is made of the reagent/ diluent mixture. A blood serum sample is then added to the cuvette. The instrument mixes the same and then performs a photometric analysis of the reaction product. Final results are displayed on the liquid crystal display 31 (and the optional printer). At the conclusion of the analysis, the instrument provides visual and audible signals to the operator to indicate that the operations are concluded. The cuvette is then removed and manually discarded. The instrument is then ready for the next analysis.

The instrument 10 is a single channel, sequential analyzer. Throughput is dependant upon the time needed for sequential tablet mixing, heating, serum mixing, and analysis time. Analysis time can be from anywhere from about 5 seconds to 10 minutes. Depending upon the mix of assays and whether or not an optional off-line mixer/heater (not shown) is used, a throughput of approximately 6-20 test results per hour may be achieved. The number of tests performed may range between 500 and 4000 per year, with a typical workload of 2000 per year.

Figure 2:
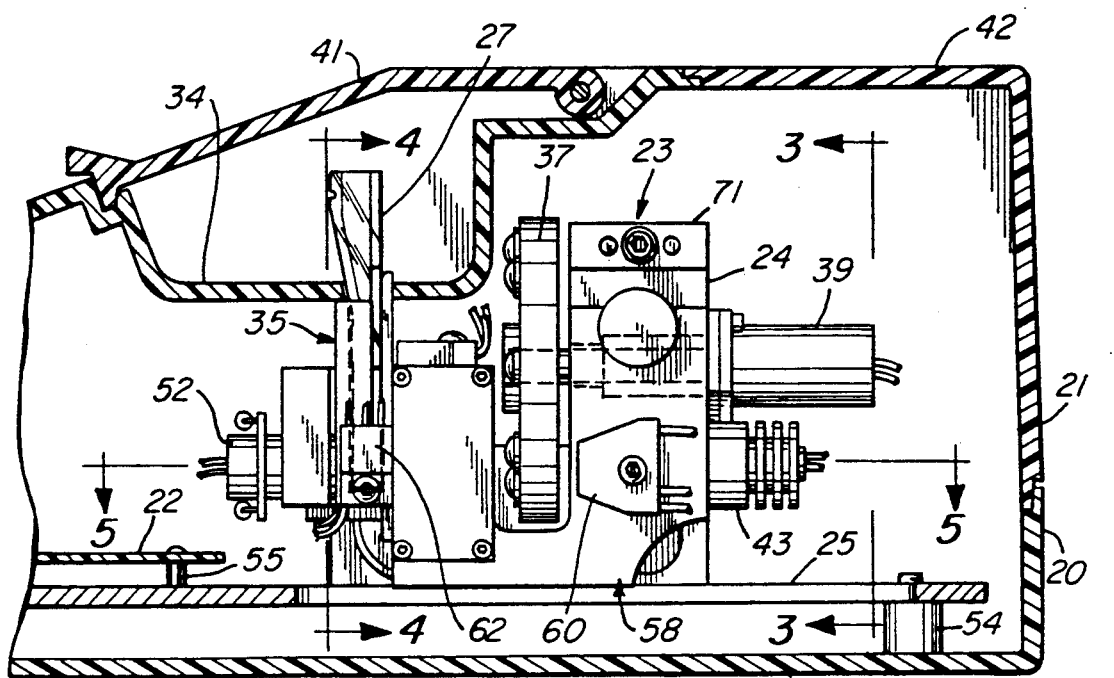
FIG. 2 is a cross sectional side view of the optical assembly within the instrument, taken along the section lines 2—2 of FIG. 1.
Figure 5:
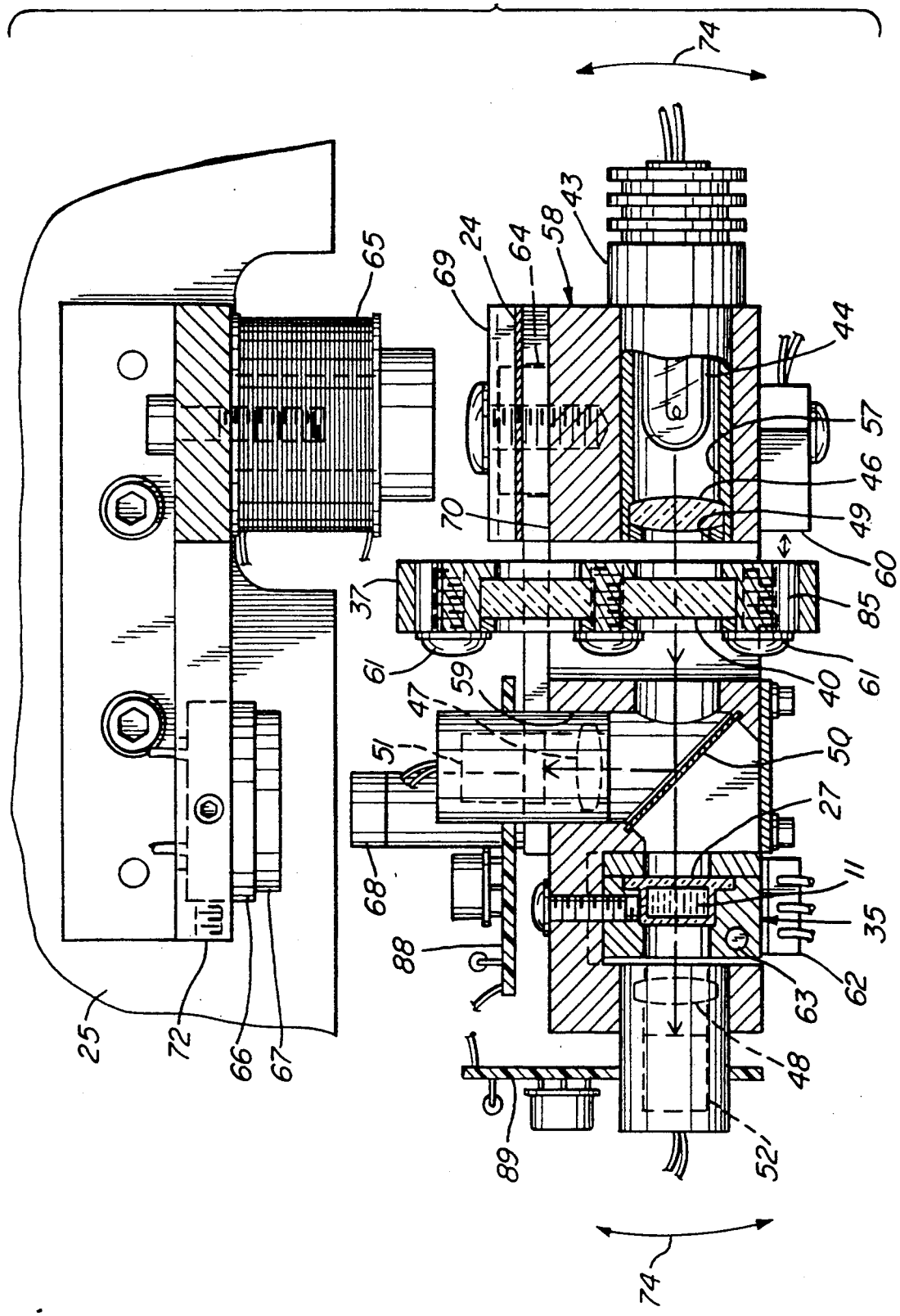
FIG. 5 is a cross-sectional view taken along the section lines 5—5 in FIG. 2 of the optical assembly and baseplate showing the electromechanical coupling therebetween.

There is one cuvette holder 35 provided in the instrument (see FIGS. 2 and 5). A cuvette 27 is disposed in the holder while the reagent tablet is dissolved, while the mixture is heated, while the reagent blank reading is taken, while the reagent and sample are mixed, and while the reagent/sample mixture is analyzed.

The instrument cabinet 19 is a clam-shell design (see FIGS. 1-2). A bottom half 20 of the cabinet holds a main PC board 22, an optical assembly 23 mounted via a leaf spring 24 to a baseplate 25, electromechanical coupling elements 26 between the optical assembly and baseplate, a power switch (not shown), a power jack and cable 28, and a port with a ribbon cable 29 connection to a printer or computer (not shown). A top half 21 of the cabinet holds a keypad 30, an alpha numeric display 31, a removable deck 34 which covers the cuvette holder 35 and provides access to a filter wheel 37, a hinged lid 41 which covers the cuvette 27, and a rear lid 42 which provides access to batteries (not shown), PROM card (not shown), filter wheel 37 and lamp 43. The cabinet exterior and interior are designed to isolate the optical and electrical elements from spilled liquids and thus prevent damage from short circuits or corrosion.

Figure 6:
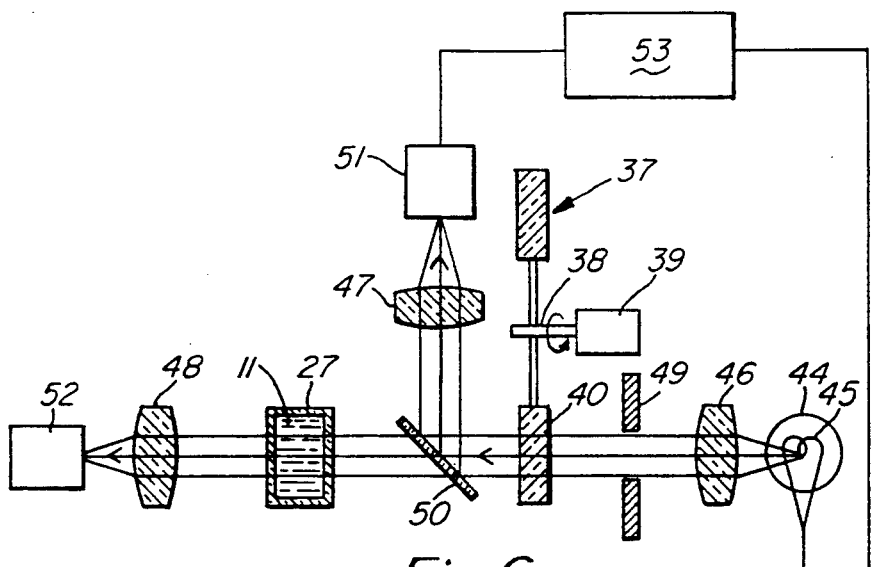
FIG. 6 is a schematic diagram of the optical assembly.

A schematic diagram of the optical assembly 23 is shown in FIG. 6. Light generated by a filament 45 in bulb 44 is focused to parallel rays by a lens 46 and an aperture 49 restricts the rays to a collimated beam of small diameter. The beam passes through a filter 40 which isolates the wavelength of light appropriate for the test being run. The filter 40 is one of a plurality of filters mounted in a filter wheel 37 which is rotated via a shaft 38 by a filter wheel motor 39. The light beam is then split into two parts by a partially reflective beam splitter 50 which reflects about 10% of the beam to a reference photodetector 51 via a lens 47 which effectively collects the light onto the photodetector 51. Ninety percent of the beam is passed to the sample 11 (in the cuvette 27) which is being analyzed. A portion is absorbed by the sample and the balance is transmitted to the sample photodetector 52 via a lens 48.

The intensity of bulb 44 is regulated by a feedback control circuit 53 (see FIGS. 9A and 9B) which stabilizes the output of the reference photodetector 51 at a constant predetermined level despite lamp and filter variations. These variations may include short term effects due to warming up of the bulb, and longer term effects such as bulb blackening or dirty optics.

Despite the feedback circuit there remains small residual variations in the reference photodetector output, typically less than 1%, which are due to the finite response speed of the feedback circuit coupled with delays in the response of the lamp to a change in applied voltage. This residual variation is compensated for in the signal processing system described hereinafter. In addition, the signal-processing compensation allows measurements to be taken before the light source output is fully stable.

The light source 43 is any sort of tungsten filament lamp, except those filled with a halogen gas. Preferably the bulb is filled with an inert gas or mixtures of such gases. The presence of an inert gas minimizes evaporation of tungsten atoms from the filament, thus allowing higher operating temperatures. Preferably, the inert gas is krypton (best) or argon, which have a lower thermal conductivity than many other inert gases. While a temperature and large filaments make them less desirable.

As shown in FIGS. 2-5, the optical assembly 23 is mounted via a leaf spring 24 to a baseplate 25 within the instrument cabinet. The baseplate is a horizontal fixed support mounted via standoffs 54 to the bottom wall 56 of the cabinet. A main PC board 22 is horizontally mounted above the baseplate via standoffs 55, toward the front end of the instrument underneath the keypad. The PC board 22 contains substantially all of the electronics, except for the photodetectors 51, 52 and their associated preamplifiers 77, 78 which are mounted on auxilliary PC boards 88, 89 disposed on the optical assembly (see FIG. 5). A user-interchangeable PROM card (not shown) fits directly into a connector on the main board 22 which contains the instructions for the various assays to be run on the instrument.

As shown in FIG. 5, the optical assembly includes a lamp 43 at one end and a sample photodetector 52 at the opposing end. The lamp is mounted in one end of a cylindrical channel 57 which extends the length of the optical assembly housing or block 58. Disposed in serial arrangement along the channel are a lens 46, aperture 49, one filter 40 of the filter wheel, beam splitter 50, cuvette 27, lens 48, and sample photodetector 52 (see also the schematic diagram of FIG. 6). A right angle branch channel 59 extends off the main channel at the beam splitter in which is disposed a lens 47 and the reference photodetector 51.

The filter wheel 37 has eight peripheral positions 86 for holding eight filters of different wavelengths. The filter wheel is driven by a DC gear motor 39. Under software control, the proper filter is selected automatically for the specific analysis to be performed. An additional photodetector 60 determines the filter wheel position by reflecting light off of shiny locating pins 85, as opposed to the black filter wheel. The individual filters are releasably attachable to the filter wheel via clamping screws 61 and are thus easily removable for cleaning or replacement.

The cuvette holder 35 is an insulated, temperature controlled, outer enclosure and is designed to hold a specifically shaped cuvette. The cuvette 27 is rectangular in cross-section and is vertically positioned within the holder. It is to be understood that this invention is not limited to a cuvette of any particular size or shape, but that a preferred embodiment is being described herein.

A photodetector 87 is provided to sense the presence or absence of the cuvette 27 and to signal appropriately to the instrument and operator. The cuvette holder 35 is designed such that a leaking cuvette will not cause a degradation of instrument performance. A heater 63 and a temperature sensor 62 are mounted adjacent the cuvette holder. The cuvette holder is designed to bring a 300 ml of 18° C. reagent tablet/solution to 37° C. within three minutes and to maintain the temperature of the liquid in the cuvette at 37°±0.3° C.

The unitized optical assembly 23 is mounted on a leaf spring 24 and is fitted with a permanent magnet 64 which reacts to an energized electromagnet 65 mounted on the instrument baseplate 25. The magnet will not deleteriously affect instrument performance in any manner. The optical assembly is programmed to shake (oscillate) during specific portions of the assay. The shaking action will dissolve the reagent tablet in 300 ml of buffer in three minutes or less. It will also insure optically complete mixing of the sample (based on a comparison with DiNapt serum substitute) with the reagent solution in 15 seconds or less. A motion detector 66 monitors the magnitude of the shaking motion and allows a microprocessor to seek and maintain the resonant frequency, thereby achieving the most effective shaking action with minimum power drain.

Figure 3:
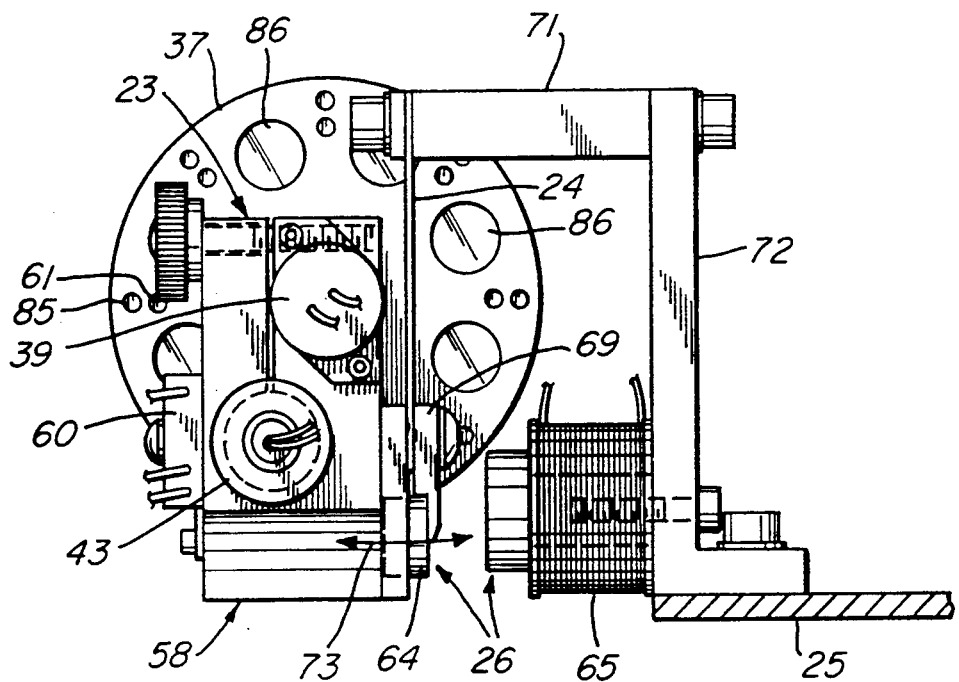
FIG. 3 is a cross sectional view from the light source end of the optical assembly, taken along the section lines 3—3 in FIG. 2, showing the leaf spring mounting and the electromechanical coupling elements between the optical assembly and the instrument baseplate.
Figure 4:
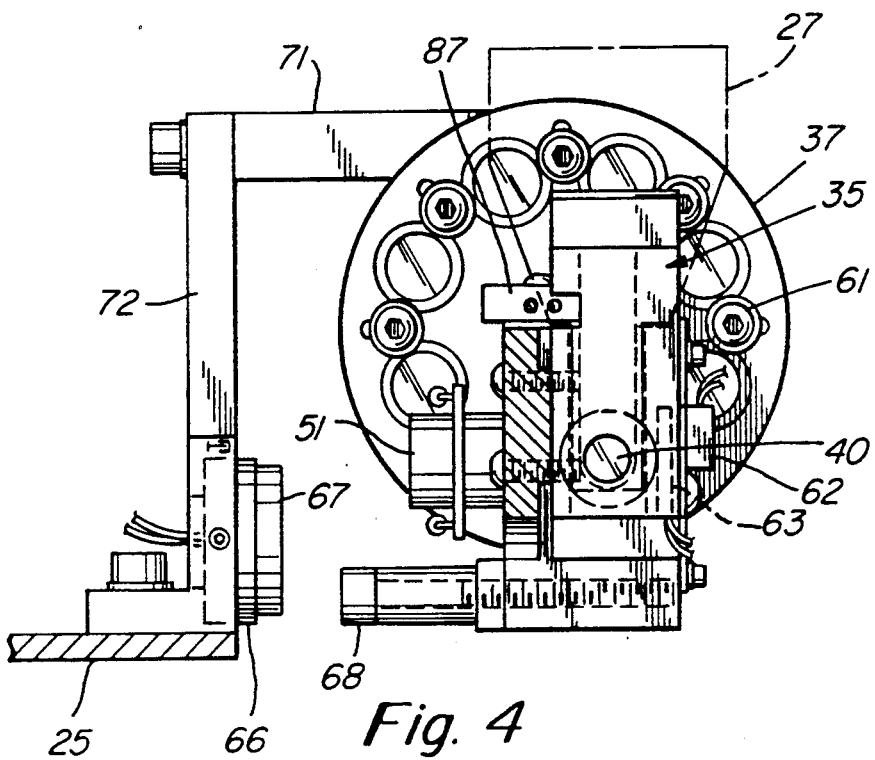
FIG. 4 is a cross sectional view from the sample photodetector end of the optical assembly (opposite end as FIG. 3), taken along the section lines 4—4 in FIG. 2.

As shown in FIGS. 3 and 5, the leaf spring 24 is vertically disposed adjacent the lamp end of the optical assembly. A clamp 69 attaches the leaf spring 24 and the adjacent permanent magnet 64 to one side 70 of the optical assembly housing 58 adjacent the lamp end. At its opposing end the leaf spring is connected to a horizontal support member 71 which in turn is connected to a fixed vertical support 72 which is connected at its lower end to the baseplate 25. The core of electromagnet 65 is horizontally mounted at the bottom of the vertical support 72 opposite the permanent magnet 64. Electromagnetic coupling between the electromagnet and permanent magnet causes an oscillatory motion of the optical assembly in the direction of the arrows 73, 74 shown in FIGS. 3 and 5. The electromagnet is activated to drive the optical assembly 23 at its resonant frequency for optimum mixing of the contents of the cuvette.

A motion detector 66 and adjacent bumper 67 (FIG. 5) are mounted on the vertical support 72 and are in alignment with a bumper post 68 mounted on the one side 70 of the optical assembly housing adjacent the sample photodetector end. The distance between the bumper post 68 and bumper 67 is selected such that the bumper post will engage the bumper between the two limit frequencies centered on the resonant frequency as hereinafter described. The motion detector is a piezoelectric element which produces a voltage signal whenever the element is mechanically deformed, i.e., when the bumper post engages the bumper. The two limit frequencies are used to determine the resonant frequency as described hereinafter.

The specifics of the lamp control circuit 53 and system processing techniques which compensate for lamp intensity variations will now be described in greater detail.

Figure 9A:
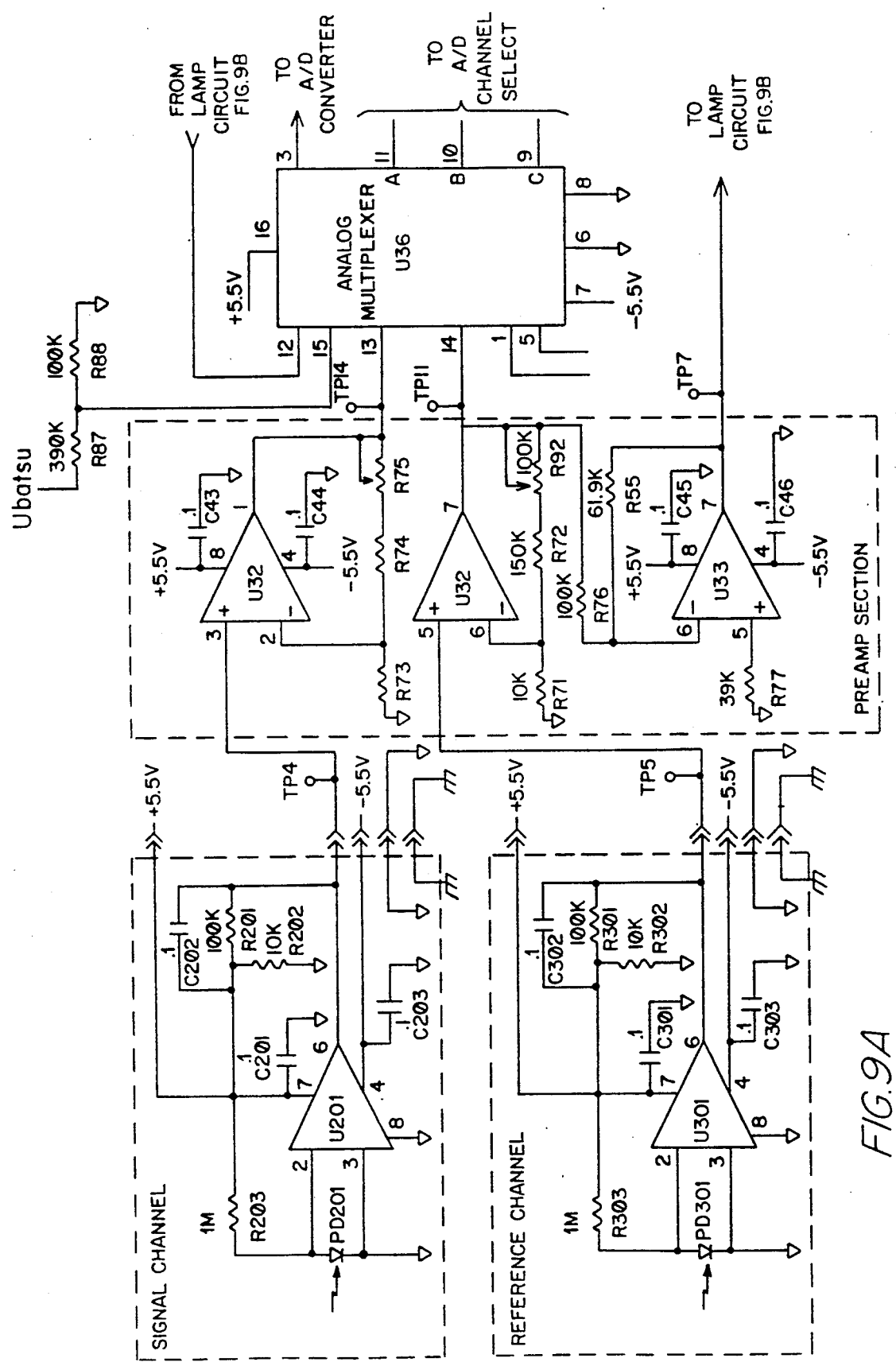
FIGS. 9A and 9B are schematic diagrams of the circuits for processing the outputs of the sample and reference photodetectors and controlling the output of the lamp.
Figure 9B:
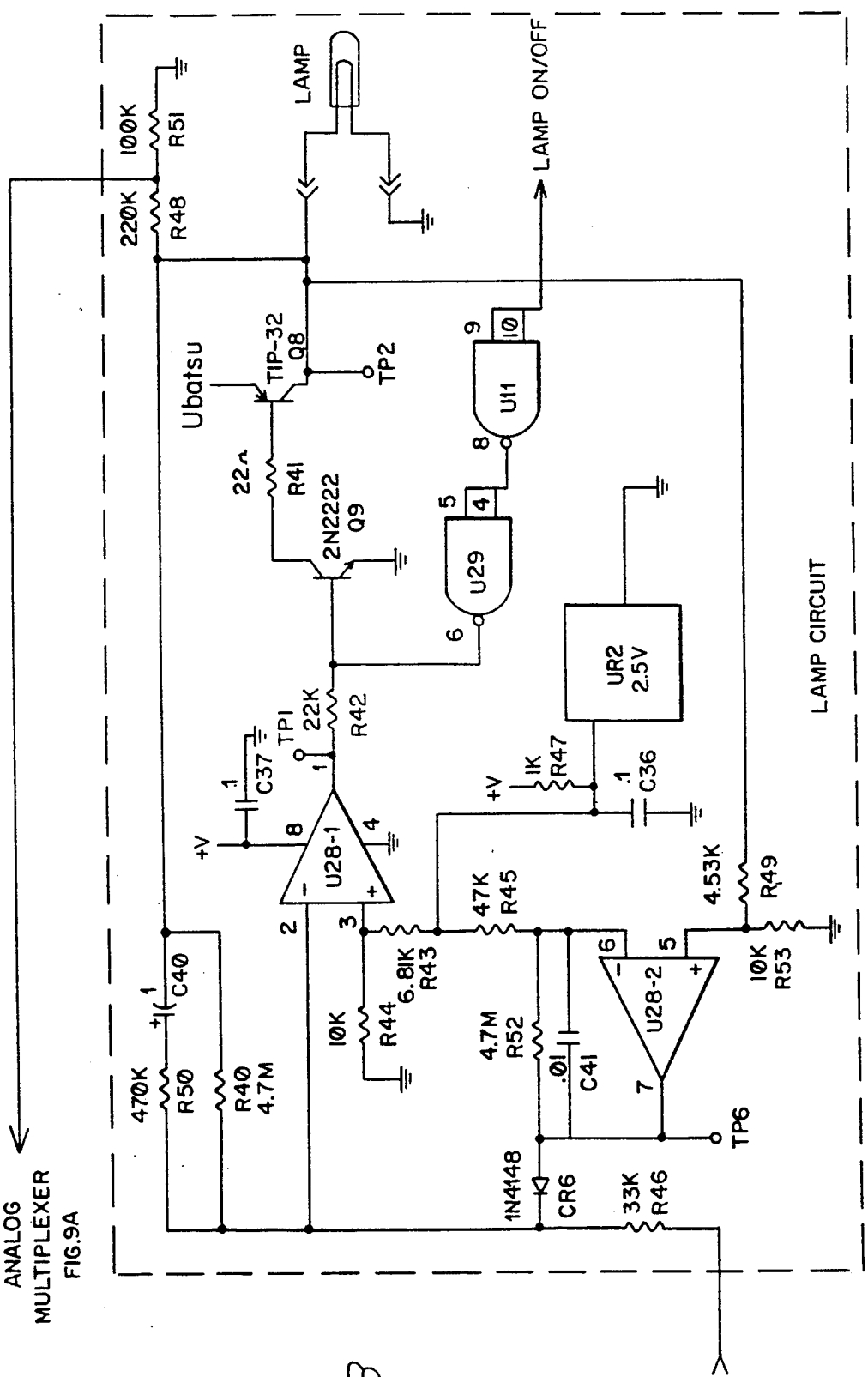
Figure 10:
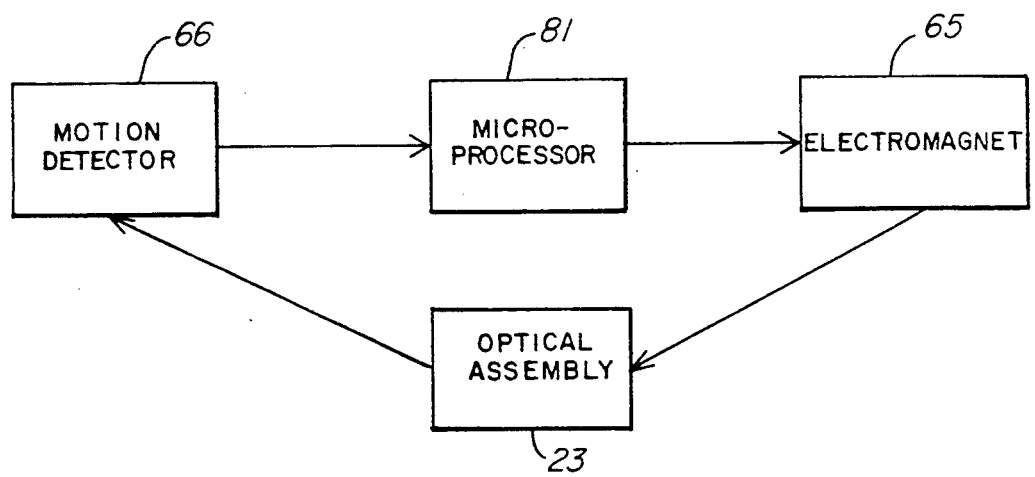
FIG. 10 is a schematic diagram of the apparatus for determining the resonant frequency of the optical assembly.

The circuit 53 for stabilizing the lamp output is shown in FIGS. 9A and 9B. The following list identifies, by manufacturer and part number, the specific components therein:

| U 28 | LM358N | National Semiconductor |
| U 29 | MM74HCO3N | Motorola |
| U 11 | MM74HCOO | Motorola |
| UR 2 | LM385BZ-2.5 | National Semiconductor |
| U 32 | TLC27L2CP | Texas Instruments |
| U 33 | TLC27L2CP | Texas Instruments |

| | | |
|---|---|---|
| U 36 | CD4051BCN | RCA |
| U 201 | AD 549 KH | Analog Devices |
| U 301 | AD 549 KH | Analog Devices |

The lamp is a krypton filled tungsten filament bulb sold under part no. L1021 by Gilway Technical Lamp, Inc., Woburn, Mass. As previously described, a portion of the lamp's light output is reflected into the reference photodetector 51 which provides an output current proportional to the light intensity. Referring to the Reference Channel portion of FIG. 9A, the current out of the reference photodetector 51 (PD301 in FIG. 9A) flows through resistor R303, creating a voltage drop across the resistor. The output of op amp U301 becomes more negative, producing a current through the divider formed by resistors R301 and R302. Once stability is achieved, the output voltage of U301, $V_{ref}$, will be $$V_{ref} = (I_{pdr})(R_{303})[(R_{301})/(R_{302}) + 1]$$

where $I_{pdr}$ is the current out of the reference photodetector.

The output of the preamplifier circuit is then further amplified by U32 and U33 before going to the lamp control circuit. When the feedback control circuit is functioning properly, the voltage at TP7 is 1.5 volts.

Referring to FIG. 9B, the preamp output TP7, which should be 1.5 volts, is compared by U28-1 to the output of voltage reference UR2 which has been divided down to 1.5 volts by R43 and R44. Operational amplifier U28-1 and transistor Q9 amplify any residual error in the preamplifier output, and control transistor Q8, which provides power to the lamp. Voltage to the lamp is thus automatically controlled so as to produce a preamplifier output voltage of 1.5 volts. Feedback resistors R50 and R40 together with capacitor C40 determine the frequency response to assure stable operation.

Gates U29 and U11 are controlled by the microprocessor to turn the lamp off when it is not needed. When the output of U29 is low, transistor Q9 is turned off, which consequently turns off the lamp. U28 2 is a voltage clamp to limit the lamp voltage to 4.0 volts, preventing premature lamp burnout. The lamp voltage is divided down and compared to the voltage reference UR2. If it goes too high, the output of U28 2 goes high forcing the preamplifier output higher than it otherwise would be. This in turn limits the drive to the lamp power transistor Q8. The only condition under which the clamp circuit would function in this way would be if there were an obstruction (e.g., dirt on a filter) which was preventing enough light from getting to the reference photodetector.

The lamp voltage is monitored by the microprocessor via the multiplexer and the AD converter. If the lamp voltage goes high enough so that the clamp has to limit the voltage, then the microprocessor will send a message to the operator via the LCD display alerting him to the need for attention to the optical system.

Figure 8:
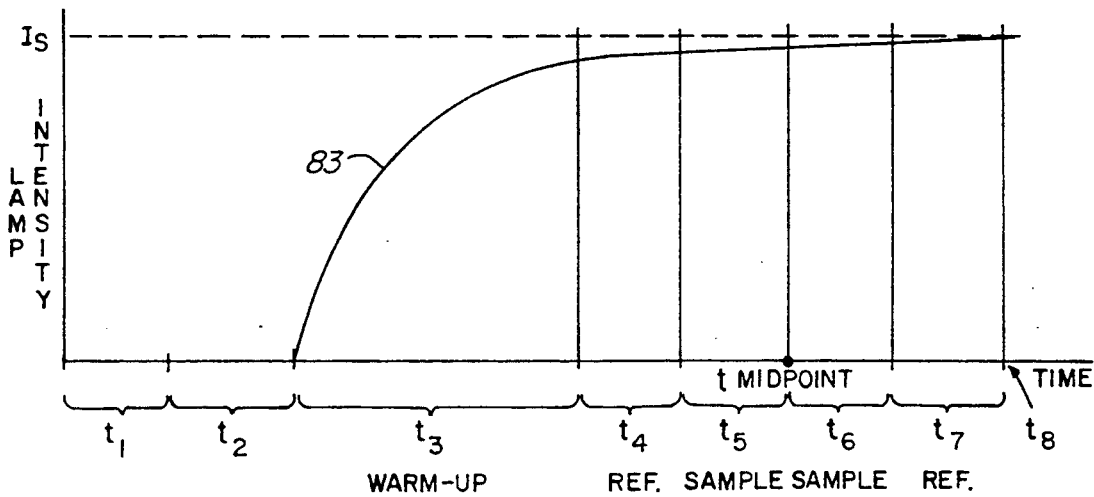
FIG. 8 is a graph of lamp intensity vs. time showing how the lamp output asymptotically approaches a stable final value and the time periods over which a series of four measurements are made.

As shown in FIG. 8, the response time of the feedback circuit is chosen so that the lamp intensity gradually increases asymptotically to the final stable value $I_s$ in a smooth exponential curve 83 whose time constant $\tau$ is typically from about 0.1 to about 0.3 seconds. Any attempt to make this approach faster results in either overshoot or oscillations, both of which defeat the method of signal processing. A second reason for the slow approach is to minimize the thermal shock associated with turn on and thus prolong the bulb's life.

Approximately three seconds after turn on, the bulb's output is considered stable enough to begin a measurement—i.e., the bulb intensity is within about 1% of its final stable value. Both a reference detector intensity $I_{ref}$ and a sample detector intensity $I_{samp}$ are determined and the ratio thereof used to calculate the absorbance $A_u$ of the sample according to the formula:

$$A_u = \log(I_{ref}/I_{samp}) + k$$

where k is a constant determined by the exact beamsplitting ratio. If $I_{ref}$ and $I_{samp}$ were read simultaneously, then $A_u$ would be independent of lamp intensity because the reference and sample intensity occur only as a ratio. While simultaneous readings can be done with more elaborate circuit elements, it increases the cost of the instrument. In contrast, this instrument uses off-the shelf, low cost circuit elements as shown in FIG. 7.

Figure 7:
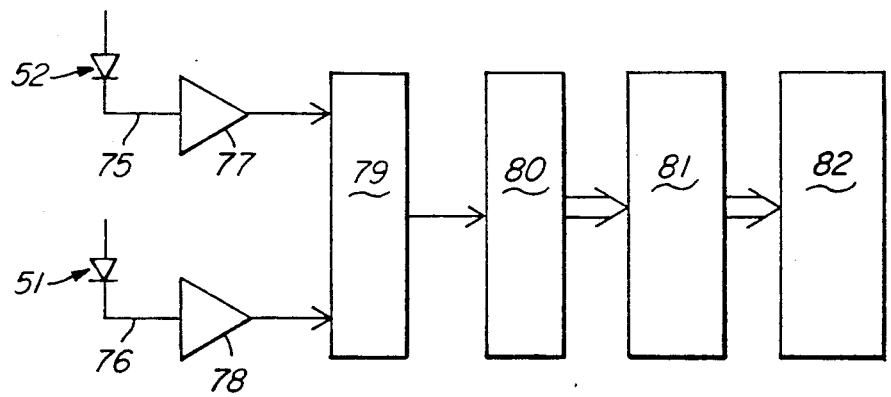
FIG. 7 is a schematic diagram of the circuit for processing the outputs of the sample and reference photodetectors.

FIG. 7 shows how the outputs 75, 76 of the sample and reference photodetectors are processed. The analog output of each of the sample and reference photodetectors 51, 52 is sent to separate preamplifiers 77, 78 and the outputs thereof are sent to a multiplexer 79. The analog output of the multiplexer is sent to an analog to digital (AD) converter 80. The digital output of the AD converter is sent to a microprocessor 81 and the digital output of the microprocessor is sent to various output devices 82.

The preamplifiers 77, 78 convert the extremely low level photodiode currents into voltages. A multiplexer 79 selects which of the two voltages is to be measured at a given time and connects it to the analog-to digital converter 80. The AD converter 80 is a dual slope integrating converter, chosen because of its low cost, high accuracy and immunity to electrical noise. It integrates the signal appearing at its input over a fixed time period, such as 0.1 seconds. All signal variations which occur in this time frame are averaged out, including any pickups from 50 Hz or 60 Hz powerlines. The output is thus an average value.

After integration is complete, the AD converter then deintegrates the signal by applying a discharging current to the integrating capacitor and times how long it takes to fully discharge. This time is proportional to the net charge accumulated by the capacitor during the integration.

In order to allow measurements to be taken before the lamp output is fully stable, and to compensate for linear variations in lamp intensity which occur over the time period at which reference and sample measurements are made, a sequence of measurements is taken about a midpoint in time preferably in the following order: reference; sample; sample; reference. After the measurements are taken, the two sample readings are averaged and the two reference readings are averaged. With the assumption that the lamp intensity changes in a linear fashion over the time during which these measurements are taking place, the result of this averaging is equivalent to having taken both measurements simultaneously at a midpoint in time.

A pictorial representation of the absorbance measurement sequence is shown in FIG. 8:

(1) Reference photodetector dark current measurement taken during time period $t_1$ (this is made while the lamp is off to establish an accurate zero point).

(2) Sample photodetector dark current measurement taken during time period $t_2$ (also made while lamp is off).

(3) Lamp turned on and allowed to warm-up and stabilize during time period $t_3$ (about 3 seconds).
(4) Reference measurement taken during time period $t_4$.
(5) Sample measurement taken during time period $t_5$.
(6) Sample measurement taken during time period $t_6$.
(7) Reference measurement taken during time period $t_7$.
(8) Lamp turned off at time $t_8$.

Each measurement requires three steps. The first step is an automatic zeroing of the A/D converter. This is an internal process within the A/D converter chip, and it proceeds for a fixed length of time, e.g., 100 milliseconds.

The second step is the charging of a capacitor with a current proportional to the voltage measured. This lasts again for a fixed length of time, e.g., 100 milliseconds. This length of time is chosen to be an integral multiple of both 50 Hz and 60 Hz line frequencies, so as to minimize the effect of noise coming over the power lines.

The third step is the deintegration step, in which the capacitor is discharged by a known constant current. The elapsed time until the capacitor voltage falls down to a preset level is proportional to the original signal voltage being measured. Component values are chosen so that the maximum deintegration time for the largest allowable signal is, for example, 200 milliseconds.

The total measurement time is the sum of all three times, or 400 milliseconds. Actually, the third step may be shorter than 200 milliseconds, so that potentially the entire process could finish in less than 400 milliseconds. However, this possibility is not realized in practice; a new measurement is never started until a full 400 milliseconds have elapsed.

The method of lamp control and signal processing described has been tested and found to have excellent results. Linearity is ±1% for an absorbance range between 0.2 and 2.0 A. The noise is less than 0.005 A at A=2. This performance is at least equivalent to that of more expensive instruments. Additional advantages are a very minimal bulb warm-up period and a projected bulb lifetime (for a krypton filled tungsten filament bulb) of longer than seven years of average use.

Another important reason for stabilizing the light incident on the sample regardless of the filter chosen is to always use the full dynamic range of the A/D converter. Thus, regardless of filter choice, if a blank solution of zero absorbance is placed in the cuvette holder, the sample detector output will be near its full scale or saturated value (approximately 2.5 volts). As samples of increasing absorbance are inserted into the cuvette, the output of the sample detector will decrease until for an A=2 sample the sample detector output will be 1/100 of its full scale amount, or 0.025 volts. If the lamp were always held at a constant voltage, regardless of filter selection, the light incident on the sample would vary widely depending on the filter chosen, owing to the fact that the lamp emits far more light in the 600–700 nm region than at 340 nm, and also because the photodetector is far more sensitive in the 600–700 nm region than at 340 nm. As an example, there might easily be a 100:1 variation in light intensity between the choice of a 600 nm filter and a 340 nm filter. If the preamplifier gain were chosen so that at 600 nm with an A=0 sample the output were 2.5 volts, then at 340 nm with an A=2 sample the output would be only 0.00025 volts. It would take a very expensive A/D converter to adequately resolve a signal over this wide a dynamic range. The present method of controlling lamp intensity avoids this problem of excessive dynamic range.

As previously described, the instrument has the ability to vigorously mix the contents of the cuvette while it is in the instrument. The entire optical assembly 23, including the cuvette holder 35, is mounted on an optical housing or block 58, and the optical block is mounted via a leaf spring 24 to the instrument baseplate 25. An electromagnet 65 mounted on the baseplate is electromagnetically coupled to a permanent magnet 64 located on the optical block and driven to vibrate the optical block at its resonant frequency. A microprocessor control is programmed to search for the correct resonant frequency and subsequently to use that frequency to obtain optimum results.

In order to achieve good mixing action, the motion of the cuvette must be correct for its particular shape, size and liquid volume. Furthermore, the exact weight and position of the elements in the optical block determines the resonant frequency. Thus, a single predetermined drive frequency would not produce the optimum resonant frequency for different optical blocks, or even the same block over a period of time.

Figure 11:
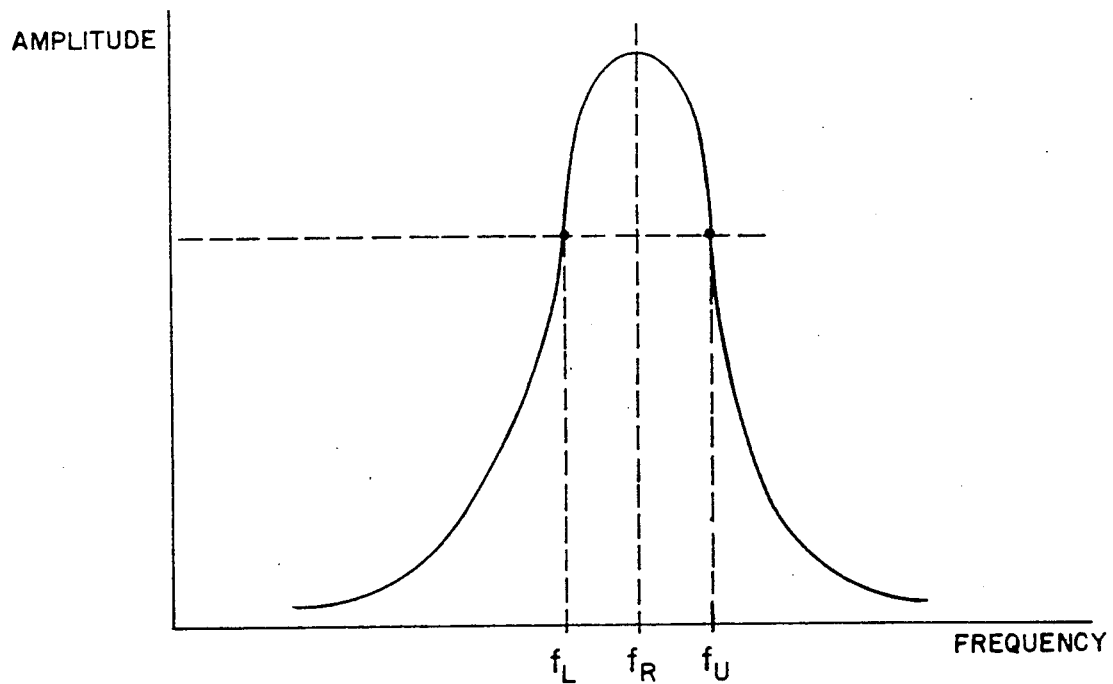
FIG. 11 is a graph of amplitude vs. frequency showing the upper and lower frequency limits detected by the motion detector for determining the resonant frequency.

In order to determine the optimum drive frequency, the microprocessor 81 goes through a search routine at the initial power up. It begins by driving the electromagnet 65 at a preset lower frequency (well below resonance) and starts slowly incrementing the frequency in small increments, e.g., 0.1 Hz. Eventually the driving frequency is close enough to resonance so that the motion detector 66 begins to detect motion. This is the lower limit frequency $f_L$ (FIG. 11). The microprocessor continues to increment the frequency until eventually the driving frequency is far enough above resonance so that the motion detector no longer detects motion. This is the upper frequency limit $f_U$. The motion detector is positioned such that for all frequencies between these two limits frequencies, the motion of the cuvette holder is adequate to mix the contents within a predetermined time limit, e.g., 15 seconds.

The microprocessor receives output signals from the motion detector between the two limits. The microprocessor contains the corresponding two limit frequencies because the microprocessor controls the drive frequency of the electromechanical coupling means. The microprocessor takes these two limit frequencies, averages them, and stores this value in memory. From that point on, each time the instrument is called upon to mix, it uses the average value stored in memory. However, each time the electromechanical coupling means is activated, the microprocessor will check to make sure that the detector 66 detects motion. If it fails to do so, the microprocessor will automatically go back into its search routine to reestablish the resonant drive frequency.

By way of example, in the preferred embodiment described herein the mass of the entire vibrating optical assembly is about 525 grams. The cuvette, made of PVC, is 0.015" thick and has a mass of 1.4 grams. The dimensions of the cuvette are 0.225" thickness, 0.325" width, and 2.12" height. The liquid volume is 300 microliters, giving a mass of about 300 milligrams. The leaf spring is made of 1095 steel, hardened to Rockwell C58, and the spring dimensions are 1.000" wide, 2.000" long, and 0.022" thick. The bumper restricts the amplitude of motion to no greater than 0.7" peak to peak. The range of exciting frequency over which the vibrating optical assembly achieves sufficient amplitude so that it can hit the bumper is typically a 0.5 Hz range. The bumper is made of a material designed to absorb the shock of the impact and not provide any rebound. It is a plastic material, no. C-1002-06PSA, from EAR Division/Cabot Corporation, Indianapolis, Ind. The resultant resonant frequency of this optical assembly is 16 Hz±1 Hz.

While it is preferred to provide resonant frequency mixing of the cuvette within the photometer, the apparatus and method for determining the resonant frequency described herein may also be used with an off-line mixer.

The following is an example of performing a glucose analysis on a blood serum sample with the instrument of this invention.

After turning on the instrument and verifying that the LCD indicates that the instrument is ready, the operator enters the identifying designation for a glucose analysis and enters the patient's ID number. The instrument will briefly self calibrate, which takes about 5 seconds. To prepare the reagent blank solution, a cuvette is filled with 300 μl of diluent. A reagent tablet is added to the cuvette, the cuvette is inserted into the instrument and the lid 41 is closed. The electromechanical coupling means is activated at the resonant frequency in order to dissolve the tablet, and the heater is activated to heat the solution to 37° C., within 2-3 minutes. The operator then adds 10 μl of a blood serum sample to the cuvette. The solution is mixed and then analyzed, which takes about 5 minutes. The results are displayed on the LCD display and are printed if the optional printer is connected. The cuvette is then removed and discarded and the operator presses the reset button to erase the results from the previous display. The instrument is now ready to begin another assay.

Although a preferred embodiment of the invention has hereinbefore been described, it will be appreciated that variations of this invention will be perceived by those skilled in the art, which variations are nevertheless within the scope of this invention as defined by the claims appended hereto.

What is claimed is:

1. In an apparatus for making a photometric determination regarding the contents of a sample, wherein light from a source of a predetermined wavelength is separated into a first portion which is sent to a reference photodetector and a second portion which is sent to a sample, the light passing through the sample being sent to a sample photodetector for making a photometric determination regarding the contents of the sample, the improved apparatus allowing a photometric measurement to be made after a reduced warm-up period and compensating for variations in the intensity of the source during the measurement, wherein the improvement comprises:

means for stabilizing the light emitted by the source to cause the source intensity to asymptotically approach a final stable value in a smooth and substantially exponential curve, wherein the stabilizing means is a feedback circuit between the reference photodetector and the light source having a time constant of from about 0.1 seconds to about 0.3 seconds; and means for processing outputs of the reference and sample photodetectors taken at different times while the source intensity approaches a final stable value and which compensates for variations in the light source intensity over the time period during which the outputs are taken.

2. In an apparatus for making a photometric determination regarding the contents of a sample, wherein light from a source of a predetermined wavelength is separated into a first portion which is sent to a reference photodetector and a second portion which is sent to a sample, the light passing through the sample being sent to a sample photodetector for making a photometric determination regarding the contents of the sample, the improved apparatus allowing a photometric measurement to be made after a reduced warm-up period and compensating for variations in the intensity of the source during the measurement, wherein the improvement comprises:

means for stabilizing the light emitted by the source to cause the source intensity to asymptotically approach a final stable value in a smooth and substantially exponential curve, wherein the stabilizing means is a feedback circuit between the reference photodetector and the light source and stabilizes the intensity of light emitted by the source to within about 1% of less of its final stable value within about 3 seconds or less;

means for processing outputs of the reference and sample photodetectors taken at different times while the source intensity approaches a final stable value and which compensates for variations in the light source intensity over the time period during which the outputs are taken.

3. In an apparatus for making a photometric determination regarding the contents of a sample, wherein light from a source of a predetermined wavelength is separated into a first portion which is sent to a reference photodetector and a second portion which is sent to a sample, the light passing through the sample being sent to a sample photodetector for making a photometric determination regarding the contents of the sample, the improved apparatus allowing a photometric measurement to be made after a reduced warm-up period and compensating for variations in the intensity of the source during the measurement, wherein the improvement comprises:

means for stabilizing the light emitted by the source to cause the source intensity to asymptotically approach a final stable value in a smooth and substantially exponential curve; and means for processing outputs of the reference and sample photodetectors taken at different times while the source intensity approaches a final stable value and which compensates for variations in the light source intensity over the time period during which the outputs are taken, wherein the processing means comprises:

means for receiving a series of four outputs taken at different times, a first pair of outputs being the outputs of the reference photodetector taken at equal times before and after a midpoint in time, a second pair of outputs being the outputs of the sample photodetector taken at equal times before and after the midpoint;

means for averaging the first pair of outputs to produce an average reference photodetector measurement and averaging the second pair of outputs to produce and average sample photodetector measurement; and means for taking a ratio of the average sample photodetector measurement and the average reference photodetector measurement to determine the absorbance characteristic of the sample as if the sample and reference photodetector measurements were taken at the same midpoint in time.

4. In an apparatus for making a photometric determination regarding the contents of a sample, wherein light from a source of a predetermined wavelength is separated into a first portion which is sent to a reference photodetector and a second portion which is sent to a sample, the light passing through the sample being sent to a sample photodetector for making a photometric determination regarding the contents of the sample, the improved apparatus allowing a photometric measurement to be made after a reduced warm-up period and compensating for variations in the intensity of the source during the measurement, wherein the improvement comprises:

means for stabilizing the light emitted by the source to cause the source intensity to asymptotically approach a final stable value in a smooth and substantially exponential curve; and means for processing outputs of the reference and sample photodetectors taken at different times while the source intensity approaches a final stable value and which compensates for variations in the light source intensity over the time period during which the outputs are taken;

wherein the light source is a tungsten filament disposed within a bulb, the bulb being filled with a gas which is unreactive with the tungsten filament and which prevents deposition of the tungsten on the interior of the bulb.

5. The apparatus of claim 4, wherein the gas is selected from the group consisting of krypton and argon.

6. In an apparatus for making a photometric determination regarding the contents of a sample, wherein light from a source is sent to a filter for alternatively selecting one of a plurality of predetermined wavelengths, the light passing through the filter being separated into a first portion which is sent to a reference photodetector and a second portion which is sent to a sample, the light passing through the sample being sent to a sample photometer for making a photometric determination regarding the contents of the sample, the improved apparatus allowing a photometric measurement to be made after a reduced warm-up period and compensating for variations in the intensity of the source during the measurement, wherein the improvement comprises:

the light source comprises a tungsten filament disposed within a bulb, the bulb being filled with a gas which is unreactive with the tungsten filament and which prevents deposition of the tungsten on the interior of the bulb;

means connecting the reference photodetector and source for stabilizing the light emitted by the source to cause the source intensity to asymptotically approach a final stable value in a smooth and substantially exponential curve for any one of the plurality of predetermined wavelengths selected by the filter; and means for processing outputs of the reference and sample photodetectors taken at different times while the source intensity approaches a final stable value and which compensates for variations in the light source intensity over the time period during which the outputs are taken.

7. In a method for making a photometric determination regarding the contents of a sample, wherein light from a source of a predetermined wavelength is separated into a first portion which is sent to a reference photodetector and a second portion which is sent to a sample, the light passing through the sample being sent to a sample photodetector for making a photometric determination regarding the contents of the sample, the improved method allowing a photometric measurement to be made after a reduced warm up period and compensating for variations in the intensity of the source during the measurement, the improved method comprising the steps of:

turning on the light source;

sending the output of the reference photodetector to a control circuit connected to the source for causing the light source intensity to asymptotically approach a final stable value in a smooth exponential curve;

after the light intensity has reached within about 1% of its final stable value, taking a series of four measurements at separate times, a first pair of measurements being the outputs of the reference photodetector taken at equal times before and after a midpoint in time, a second pair of measurements being the outputs of the sample photodetector taken at equal times before and after the midpoint;

averaging the first pair of measurements to produce an average reference photodetector measurement and averaging the second pair of measurements to produce an average sample photodetector measurement; and taking a ratio of the average sample photodetector measurement and the average reference photodetector measurement to determine the absorbance characteristic of the sample as if the sample and reference photodetector measurements were taken at the same midpoint in time.

8. In a method for making a photometric determination regarding the contents of a sample, wherein light from a source of a predetermined wavelength is separated into a first portion which is sent to a reference photodetector and a second portion which is sent to a sample, the light passing through the sample being sent to a sample photo-detector for making a photometric determination regarding the contents of the sample, the improved method allowing a photometric measurement to be made after a reduced warm-up period and compensating for variations in the intensity of the source during the measurement, the improved method comprising the steps of:

turning on the light source;

causing the light source intensity to asymptotically approach a final stable value in a smooth and substantially exponential curve;

processing outputs of the reference and sample photodetectors taken at different times while the source intensity approaches a final stable value and compensating for variations in the source intensity over the time period during which the outputs are taken;

wherein the light source comprises a tungsten filament disposed within a bulb, the bulb being filled with a gas which is unreactive with the tungsten filament and which prevents deposition of the tungsten on the interior of the bulb.

9. In a method for making a photometric determination regarding the contents of a sample, wherein light from a source of a predetermined wavelength is separated into a first portion which is sent to a reference photodetector and a second portion which is sent to a sample, the light passing through the sample being sent to a sample photo-detector for making a photometric determination regarding the contents of the sample, the improved method allowing a photometric measurement to be made after a reduced warm-up period and compensating for variations in the intensity of the source during the measurement, the improved method comprising the steps of:

turning on the light source;

causing the light source intensity to asymptotically approach a final stable value in a smooth and substantially exponential curve;

processing outputs of the reference and sample photodetectors taken at different times while the source intensity approaches a final stable value and compensating for variations in the source intensity over the time period during which the outputs are taken;

wherein the source intensity is caused to asymptotically approach a final stable value by providing a feedback circuit connecting the source and reference photodetector having a time constant of from about 0.1 seconds to about 0.3 seconds.

10. In a method for making a photometric determination regarding the contents of a sample, wherein light from a source of a predetermined wavelength is separated into a first portion which is sent to a reference photodetector and a second portion which is sent to a sample, the light passing through the sample being sent to a sample photo-detector for making a photometric determination regarding the contents of the sample, the improved method allowing a photometric measurement to be made after a reduced warm-up period and compensating for variations in the intensity of the source during the measurement, the improved method comprising the steps of:

turning on the light source;

causing the light source intensity to asymptotically approach a final stable value in a smooth and substantially exponential curve;

processing outputs of the reference and sample photodetectors taken at different times while the source intensity approaches a final stable value and compensating for variations in the source intensity over the time period during which the outputs are taken;

wherein the intensity of light emitted by the source is stabilized to within about 1% or less of its final stable value within about three seconds or less.

11. In a method for making a photometric determination regarding the contents of a sample, wherein light from a source of a predetermined wavelength is separated into a first portion which is sent to a reference photodetector and a second portion which is sent to a sample, the light passing through sample being sent to a sample photo-detector for making a photometric determination regarding the contents of the sample, the improved method allowing a photometric measurement to be made after a reduced warm-up period and compensating for variations in the intensity of the source during the measurement, the improved method comprising the steps of:

turning on the light source;

causing the light source intensity to asymptotically approach a final stable value in a smooth and substantially exponential curve;

processing outputs of the reference and sample photodetectors taken at different times while the source intensity approaches a final stable value and compensating for variations in the source intensity over the time period during which the outputs are taken;

wherein the processing of outputs of the reference and sample photodetectors includes:

processing a series of four measurements taken at different times, a first pair of measurements being the outputs of the reference photodetector taken at equal times before and after a midpoint in time, the second pair of measurements being the outputs of the sample photodetector taken at equal times before and after the midpoint, averaging the first pair of measurements to produce an average reference photodetector measurement and averaging the second pair of measurements to produce an average sample photodetector measurement, and, taking a ratio of the average sample photodetector measurement and the average reference photodetector measurement to determine the absorbance characteristic of the sample as if the sample and reference photodetector measurements were taken at the same midpoint in time.

* * * * *

UNITED STATES PATENT AND TRADEMARK OFFICE
CERTIFICATE OF CORRECTION

PATENT NO. : 5,092,677
DATED      : March 3, 1992
INVENTOR(S) : Richard Curtis

It is certified that error appears in the above-identified patent and that said Letters Patent is hereby corrected as shown below:

Col. 5, line 5, after "a" insert --vacuum "filled" lamp may be used, their low color--.

Col. 9, line 16, after "length" insert --being--.

Col. 12, line 23, delete "of" (first occurrence) and substitute --or--.

Col. 16, line 9, after "through" insert --the--.

Signed and Sealed this

Fourth Day of May, 1993

Attest:

MICHAEL K. KIRK

*Attesting Officer*    Acting Commissioner of Patents and Trademarks